United States Patent [19]

Müller et al.

[11] Patent Number: 5,672,763
[45] Date of Patent: Sep. 30, 1997

[54] PROCESS FOR THE PREPARATION OF 2-SUBSTITUTED CYCLOPENTANONES

[75] Inventors: Nikolaus Müller, Monheim; Thomas Essert, Overath, both of Germany

[73] Assignee: Bayer Aktiengesellschaft, Leverkusen, Germany

[21] Appl. No.: 668,959

[22] Filed: Jun. 21, 1996

[30] Foreign Application Priority Data

Jun. 28, 1995 [DE] Germany .............. 195 23 448.0

[51] Int. Cl.[6] .................................................. C07C 45/45
[52] U.S. Cl. .......................... 568/355; 568/338; 568/346
[58] Field of Search ............................ 568/338, 346, 568/355

[56] References Cited

FOREIGN PATENT DOCUMENTS 2341591  9/1977  France .

OTHER PUBLICATIONS

Barco et al; "synthesis"; p. 316 1973.
Huckel et al; "Chemische Berichte"; pp. 202–206 1974.
House; "Modern Synthetic Reactions"; Second Edition; pp. 740–742 and pp. 513–515 1972.
Synthesis, Nr. 12, Dec. 1983, Seiten 996–997, XP000616229 Henerson, D., et al.: "A Quick and Efficient Route to 2-Substituted Cyclopentanones and Cyclohexanones".
V.R. Mayer, et al., Eine vereinfachte präparative Darstellung der Cyclopentanon-o-carbonsäureester, Journal für Praktische Chemie, 4th series, vol. 9, pp. 43–45, (1959).
W. Hückel, et al., cis–und trans–1–Methyl–cyclopentanol–(2), Chemische Berichte, 80, pp. 202–206, (1947).
K. Sisido, et al., An Improved Procedure for the Preparation of 2-Alkyl-5-carbethoxycyclopentanone, The Journal of Organic Chemistry, vol. 29, pp. 2781–2782, (1964).
S.E. Cremer, et al., Syntheses of Substituted Phosphetanes and Related Derivatives, The Journal of Organic Chemistry, vol. 32, pp. 4066–4070, (1967).

A. Barco, et al., A Facile Alkylation of Ethyl 2–Oxocyclopentane–carboxylate, International Journal of Methods in Synthetic Organic Chemistry, p. 316, (1973).
H.E. Zaugg, et al., Specific Solvent Effects in the Alkylation of Enolate Anions. I. The Alkylation of Sodiomalonic Esters with Alkyl Halides, pp. 2895–2903, (1960). Jacs.
M.V. Rysselberge, Préparation et étude de quelques composés cyclopentaniques 1. 2. diméthylés, Bull. Soc. Chim. Belg., 35, pp. 311–328. (1922).
H.–G. Blanc, et al., Sur une nouvelle métho le de cyclisation des acides adipiques et pimêliques substitués, C.R., 144, 1356–1358, (1907). (Academic Des Sciences).
G. Chavanne, et al., Contribution A L'étude des Composés Cyclopentaniques. Nouvelle Préparation du 1.2 Diméthylcyclopentane, Tome 37, No. 4, pp. 141–152, (1928). (Bulletin de la Societe Chimique de Belgique).
G.A. Lutz, et al., Studies in the Methylcyclopentane Series. II. Preparation and Reactions of Methylcyclopentenes[1], The Journal of the American Chemical Society, vol. 70, pp. 4139–4142, (1948).
M. Tiffeneau, et al., Mémoires et Communications, Académie des Sciences, C.R., 209, pp. 449–453, (1939).
P.D. Bartlett, et al., Cis–and Trans–Chlorohydrins of Δ[1]–Methylcyclopentene, p. 2785, (1934), Jacs.
J.–G. Rodriguez, et al., Alkylation of Cycloalkano[b]indoles via Indolylmagnesium Salts: Synthesis of 3H–Indoles and Oxidative Rearrangement to Spiro[cycloalkane-1,2'–indolin]–3'–ones, J. Heterocyclic Chem., vol. 28, pp. 1293–1299, (1991).

*Primary Examiner*—C. Warren Ivy
*Assistant Examiner*—Sreeni Padmanabhan
*Attorney, Agent, or Firm*—Sprung Horn Kramer & Woods

[57] ABSTRACT

2-Substituted cyclopentanones are prepared by reacting adipic ester with an alkoxide in the presence of an inert solvent, thus obtaining a salt of the cyclopentanone-2-carboxylic ester, alkylating this without isolation, thus obtaining a 2-alkyl-cyclopentanone-2-carboxylic ester and, without isolation, hydrolysing and decarboxylating this by treatment with an acid and heating.

9 Claims, No Drawings

PROCESS FOR THE PREPARATION OF 2-SUBSTITUTED CYCLOPENTANONES

The present invention relates to a process for the preparation of 2-substituted cyclopentanones, in particular 2-methylcyclopentanone, from dialkyl adipates.

It is already known to prepare 2-substituted cyclopentanones by alkylation of cyclopentanone-2-carboxylic esters and subsequent hydrolysis and decarboxylation. This process suffers from some disadvantages. Starting from dialkyl adipates, the process has three stages and, even in the best processes described in the literature, gives yields of only approximately 40 to 45% of theory. Thus, the cyclization in the case of the ethyl ester leads to 70 to 78% isolated yield, and in the case of the methyl ester to 68 to 74% isolated yield (see J. prakt. Chem. 4th Series, Volume 9, page 43 (1959)). The subsequently alkylation, e.g. with methyl bromide, to give the methyl 2-methylcyclopentanone-2-carboxylate proceeds in a yield of approximately 70% of theory, and the subsequent hydrolysis and decarboxylation in a yield of approximately 80% of theory, so that a yield of at most 42% of theory results, based on dialkyl adipate used (see Chem. Ber. 80, 202 (1974)).

The reason for the low yield is the reversibility of the cyclization in the first step and the cleavage occurring for the same reasons due to the auxiliary base alkoxide in carbanion formation in the alkylation step α-Alkyladipic ester is formed by the reversible cleavage, which compound itself cyclizes to give the undesired 5-alkyl-cyclopentanone-2-carboxylic ester (see J. Org. Chem. 29, 2782 (1964)).

Further reductions in yield occur owing to O-alkylations of the mesomeric enolate ion, the extent of which greatly depends on the alkali metal counter ion, the solvent and the nature of the alkylation agent. Thus precisely the inexpensive, frequently used alkyl chlorides and the alkyl sulphates lead to increased formation of O-alkyl derivatives which, with vigorous acidic hydrolysis and subsequent decarboxylation, give cyclopentanone, so that in the isolation, which is usually carried out by distillation, increased separation effort becomes necessary. Therefore, in the alkylation reaction, the expensive alkyl bromides and alkyl iodides, which require complex occupational safety precautions, are generally used.

Another disadvantage in these processes is the marked water solubility of the end products, which is particularly pronounced in the case of 2-methylcyclopentanone. This means that the products have to be laboriously isolated by multiple extraction from the aqueous reaction mixture and the organic extracts have to be dried and distilled. The remaining aqueous phase is contaminated by organic substances and requires special work-up and disposal.

For the alkylation of the 2-carboalkoxy-cyclopentanone with the corresponding alkyl halide, dipolar aprotic solvents such as dimethyl sulphoxide (J. Org. Chem. 32, 4067 (1967)) and acetone (SYNTHESIS 1973, 316) are described as advantageous in the literature, because in the nonpolar solvents otherwise conventional, such as benzene or toluene, higher molecular aggregates of the ion pairs are present, which contain considerably less free enolate ion and thus react considerably less favourably (see I. Am. Chem. Soc. 82, 2895 (1960)).

Here too, alkyl iodides or alkyl bromides have to be used, the proportion of O-alkylation being considerably higher in the case of bromide. When alkyl chlorides are used, still higher O-alkylation is to be expected, which makes the process even less economic. Furthermore, a specific reaction with potassium salts of the cyclopentanone-carboxylic ester is described, which has the consequence that the cyclization has to be carried out with the considerably more expensive potassium alkoxides, in order to remain with the single-stage variant. Otherwise, the necessary solvent change makes the two-stage process even more uneconomic. Employing the dipolar, aprotic solvents generally includes the following work-up variant: after the reaction is completed, the alkylation batch is diluted with water and the product is extracted by a nonpolar solvent such as ether or hydrocarbons. As already discussed above, the polarity of the products requires a multiple extraction, the recovery of the solvent used is very complex because of their complete miscibility with water and highly organically polluted wastewaters are generally formed.

The hydrolysis of 2-alkylcyclopentanone-2-carboxylic esters can only proceed under acid conditions, since under alkaline conditions the side reaction of acid cleavage (=ring opening) becomes too pronounced. Strong acids must be used in the acid hydrolysis in order to achieve a reasonable reaction time. Thus, e.g., dilute perchloric acid (see Ber. 80, 202 (1974)) or concentrated hydrochloric acid (see BI. Soc. chim. Belg. 35, 315) is used, both of which, because of their high price and more highly corrosive properties, are less expedient than dilute sulphuric acid.

In addition to the most common processes described above, there are a number of further processes for the preparation of 2-alkylcyclopentanones, especially 2-methylcyclopentanone.

For example, the cyclisation of α-methyladipic acid to give the anhydride followed by the thermal decomposition thereof (see C.r. 144, 1357), the distillation of the calcium salt of this acid and, the direct alkylation of cyclopentanone, which, however, leads to a virtually inseparable product mixture of mono-, di- and trimethylcyclopentanones and only proceeds with strong auxiliary bases, for example sodium amide.

From 1-methylcyclopentene oxide 2-alkylcyclopentanones can be obtained, for example, by treatment with Grignard compounds (see Soc. Chim. Belg. 37, 151), with performic acid/sulphuric acid (see A.m. Soc. 70, 4139 (1948)) or by passing the vapour over aluminium oxide at 300° C.

2-Chloro-1-methyl-cyclopentan-1-ol can also be reacted with Grignard compounds (see C.r. 209, 449 (1939)) or treated with alkali (see A.m. Soc. 96, 2785 (1934)).

Various 2-alkylidene-cyclopentanones can also be reduced.

All of these processes start from poorly available starting materials, use reagents which may be handled industrially only with difficulty and are in many cases unselective and of low yield. As a selective method, there is, further, the alkylation of 1-pyrrolidinocyclopentene (see J. Heterocycl. Chem. 28, 1293 (1991)), but here also, in the in total 3-stage synthesis, a yield of only 49% of theory is obtained, based on cyclopentanone, which itself must again be prepared from adipic esters.

A process has now been found for the preparation of 2-substituted cyclopentanones of the formula

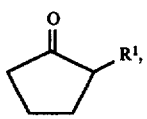 (I)

in which

R$^1$ represents straight-chain or branched $C_1$–$C_6$-alkyl, $C_3$–$C_7$-cycloalkyl or unsubstituted or halogen-substituted $C_7$–$C_{12}$-aralkyl, which is characterized in that an adipic ester of the formula

in which
the two $R^2$ are identical or different and each represent straight-chain or branched $C_1$–$C_{10}$-alkyl, $C_7$–$C_{12}$-aralkyl which may optionally be substituted by up to 3 identical or different substituents selected from the group consisting of the halogens and the $C_1$–$C_6$-alkyl, $C_1$–$C_6$-alkoxy and nitro groups, or $C_6$–$C_{10}$-aryl which may optionally be substituted by up to 3 identical or different substituents selected from the group consisting of the halogens and the $C_1$–$C_6$-alkyl, $C_1$–$C_6$-alkoxy and nitro groups, is reacted in the presence of an inert solvent with an alkoxide of the formula (III)

in which
M represents an alkali metal or an alkaline earth metal,
$R^3$ represents $C_1$–$C_{10}$-alkyl, $C_3$–$C_{10}$-cycloalkyl or $C_7$–$C_{12}$-aralkyl and
n, depending on the valency of M, represents 1 or 2, a salt of the cyclopentanone-2-carboxylic ester of the formula (IV) is thus obtained

in which
$R^2$ has the meaning given under formula (II), and
M represents one equivalent of an alkali metal or alkaline earth metal, this, without isolation, is alkylated with an alkylating agent of the formula (V),

in which
$R^1$ has the meaning given under formula (I) and
X represents halogen, $C_1$–$C_6$-alkylsulphonate, or $C_6$–$C_{10}$-arylsulphonate which may optionally be substituted by up to two $C_1$–$C_4$-alkyl groups, a 2-alkyl-cyclopentanone-2-carboxylic ester of the formula (VI) is thus obtained

in which
$R^2$ has the meaning given under formula (II) and
$R^1$ has the meaning given under formula (I),
and this, without isolation, is hydrolysed and decarboxylated by treating it with an acid and heating.

Halogen preferably represents chlorine or bromine, in particular chlorine.

Preferred adipic esters of the formula (II) are those in which the two $R^2$ radicals are identical and represent straight-chain or branched $C_1$–$C_6$-alkyl, benzyl which may optionally be substituted by up to two substituents selected from the group consisting of the halogen atoms and the $C_1$–$C_4$-alkyl groups, or phenyl which may optionally be substituted by up to two substituents selected from the group consisting of the $C_1$–$C_4$-alkyl groups and the nitro group.

Particular preference is given to adipic esters of the formula (II) in which the two $R^2$ radicals are identical and represent straight-chain $C_1$–$C_4$-alkyl. Special preference is given to dimethyl adipate and diethyl adipate.

Preferred alkoxides of the formula (III) are those in which M represents sodium, potassium, lithium, calcium or magnesium and $R^3$ represents straight-chain or branched $C_1$–$C_6$-alkyl, $C_3$–$C_7$-cycloalkyl or benzyl. Particular preference is given to sodium methoxide, potassium methoxide, calcium methoxide and magnesium methoxide, sodium ethoxide, potassium ethoxide, calcium ethoxide and magnesium ethoxide, sodium n-propoxide, potassium n-propoxide, calcium n-propoxide and magnesium n-propoxide, sodium i-propoxide, potassium i-propoxide, calcium i-propoxide and magnesium i-propoxide, sodium n-butoxide, potassium n-butoxide, calcium n-butoxide and magnesium n-butoxide, sodium i-butoxide, potassium i-butoxide, calcium i-butoxide and magnesium i-butoxide, sodium sec-butoxide, potassium sec-butoxide, calcium sec-butoxide and magnesium sec-butoxide, sodium t-butoxide, potassium t-butoxide, calcium t-butoxide and magnesium t-butoxide, and to sodium pentoxide and potassium pentoxide, sodium hexoxide and potassium hexoxide, sodium cyclopentoxide and potassium cyclopentoxide, sodium cyclohexoxide and potassium cyclohexoxide, and sodium benzoxide and potassium benzoxide. Special preference is given to sodium methoxide and potassium methoxide, sodium ethoxide and potassium ethoxide, sodium i-propoxide and potassium i-propoxide, and sodium t-butoxide and potassium t-butoxide.

Inert solvents which are suitable for the reaction of the adipic ester with the alkoxide are, for example, aliphatic and aromatic hydrocarbons having boiling points of at least 80° C. (at atmospheric pressure). Those which may be mentioned by way of example are: heptanes, octanes, nonanes, decanes, isododecanes, benzene, toluene, cumenes, xylenes, di- and triisopropylbenzenes and halogen-and/or $C_1$–$C_4$-alkoxy-substituted aromatic hydrocarbons such as chlorobenzene, dichlorobenzenes, trichlorobenzenes, anisole, phenetole and phenyl isopropyl ether. Any mixtures of these solvents may also be used.

To the above-described solvents can optionally be added dipolar, aprotic solvents, for example dimethyl sulphoxide, tetramethylenesulphone, di-$C_1$–$C_6$-(cyclo)-alkyl-formamides, N-$C_1$–$C_6$-alkylpyrrolidones, -piperidones and/or -caprolactams, tetra-$C_1$–$C_6$-alkylureas and N,N'-dimethylethylene- and N,N'-dimethylpropyleneurea. The proportion of dipolar, aprotic solvents in the total of solvents used can be, e.g., 0 to 50% by weight. Preferably, this proportion is 0 to 20% by weight, very particularly preferably, no dipolar aprotic solvent is present or its proportion is 0.01 to 10% by weight.

Based on 1 mol of adipic ester of the formula (II), e.g., 500 to 5000 ml of solvent can be used. Preferably, this mount is 800 to 3000 ml, in particular 1000 to 2000 ml.

In the reaction with the adipic ester of the formula (II), the alkoxide of the formula (III) can be used, e.g., as dry, preferably finely pulverulent, solid or as solution in the alcohol underlying the respective alkoxide. Preferably, the procedure is carded out in such a manner that the alkoxide is used in solution in the alcohol underlying the respective alkoxide and the alcohol is distilled off before the reaction with the adipic ester of the formula (II) starts to a significant extent. In this manner, a finely distributed suspension of the alkoxide in the reaction mixture is formed, which leads to particularly good results. The handling of dust-forming and hygroscopic solid alkoxides is thus also avoided, which, for this reason and because of their corrosive action, would require special occupational safety precautions.

Based on 1 mol of adipic ester of the formula (II), for example, 0.1 to 10 equivalents of an alkoxide of the formula (III) can be used. In this connexion, 1 mol of an alkoxide of the formula (III) where M=an alkali metal corresponds to one equivalent and 1 mol of an alkoxide of the formula (III) where M=an alkaline earth metal corresponds to two equivalents. Preferably, 0.5 to 2 equivalents of alkoxide are used per mol of adipic ester, in particular, 0.95 to 1.05 equivalents of alcoholate are used per mol of adipic ester.

The adipic ester can be reacted, eg. at temperatures in the range 80° to 200° C. Preference is given to temperatures in the range 100° to 150° C. Particularly preferably, the boiling temperature of the particular inert solvent used is employed. It is advantageous to distill off continuously the alcohol formed in the reaction of the adipic ester with the alkoxide.

In order to ensure good stirrability during the entire course of the reaction, it may if appropriate be necessary, during the reaction, to add additional inert solvent and/or dipolar, aprotic solvents of the type described above.

If the alcohol formed in the reaction of the adipic ester with the alkoxide has not already been distilled off during the reaction, it is distilled off after the reaction is completed. The virtually alcohol-free reaction mixture which contains the salt of the cyclopentanone-2-carboxylic ester formed, of the formula (IV), is then reacted with an alkylating agent of the formula (V).

Preferred alkylating agents of the formula (V) are those in which $R^1$ represents methyl, ethyl, n-propyl, i-propyl, benzyl, 4-chlorobenzyl or 4-fluorobenzyl and X represents chlorine, bromine or p-tolylsulphonate. Particularly preferably, $R^1$ represents methyl, ethyl, i-propyl or 4-chlorobenzyl and X represents chlorine. In particular, methyl chloride is used.

The alkylation can be performed in the same reaction vessel in which the adipic ester was reacted with the alkoxide. If volatile alkylating agents of the formula (V) are used, it is advantageous to work under pressure or in a closed vessel. The mixture containing the salt of the cyclopentanone-2-carboxylic ester of the formula (IV) can then, if appropriate, be transferred into a reaction vessel suitable for work under pressure.

Based on 1 mol of adipic ester of the formula (II) originally used it is possible to use, for example, 1 to 20 mol of an alkylating agent of the formula (V). Preferably, this amount is 1 to 10 mol, in particular 1 to 5 mol.

The reaction temperature for the alkylation can be, for example, in the range 0° to 250° C. Preferably, it is in the range 20° to 200° C., in particular in the range 50° to 160° C. The particular temperature which is optimal for a particular alkylating agent can readily be determined, if desired, by a routine series of tests.

It is advantageous to remove the solvent or solvents and any excess alkylating agent present from the reaction mixture, e.g. by distillation, after the alkylation.

Isolation of the 2-alkyl-cyclopentanone-2-carboxylic ester of the formula (VI) formed is not necessary.

Strong organic and inorganic acids, for example, are suitable for treating the 2-alkyl-cyclopentanone-2-carboxylic ester of the formula (VI) with an acid. Preference is given to hydrobromic acid, sulphuric acid, alkylsulphonic acids and arylsulphonic acids. Particular preference is given to sulphuric acid.

The acids are expediently used in the form of aqueous solutions, e.g. as 5 to 99% strength by weight aqueous solutions. Preferably, the concentration of the acids is between 10 and 80% by weight, in particular between 20 and 50% by weight.

Based on 1 mol of the adipic ester of the formula (II) originally used, for example 1 to 10, preferably 1 to 5, equivalents of acid can be used.

The hydrolysis and decarboxylation can be carried out, e.g., at temperatures in the range 50° to 150° C. Preferably, the boiling point of the aqueous reaction mixture is employed.

The prepared 2-substituted 2-cyclopentanone of the formula (I) can be isolated from the reaction mixture, e.g., by azeotropic distillation.

A preferred embodiment of the process of the invention is carried out as follows:

Inert solvent and alcoholic alkoxide solution are introduced. Adipic ester is then added and during its reaction with the alkoxide the excess alcohol and the alcohol formed are distilled off. After this reaction is complete, alkylating agent is added and, after alkylation is complete, the inert solvent is distilled off. Strong aqueous acid is added to the residue and the mixture is refluxed. 2-Substituted cyclopentanone is then isolated from the reaction mixture by azeotropic distillation.

The process of the invention permits the preparation of 2-substituted cyclopentanones of the formula (I) from adipic esters of the formula (II) without isolation of the intermediates, without drying steps, without multiple removal of solvents, without solvent change and without complex separation operations. The yield in this case is very high, generally above 80% of theory. The process of the invention is therefore energy-saving and particularly economic. 2-Substituted cyclopentanones of the formula (I) are valuable intermediates for the preparation of pesticides, especially fungicides (see, e.g., EP-329 397, EP-A 378 953 and EP-A 537 909). They can also be used as such, or after further conversion, as perfumes or flavourings.

EXAMPLES

Example 1

348.4 g of dimethyl adipate, 381 ml of 30% strength by weight sodium methoxide solution in methanol and 2884 ml of toluene are introduced into a 3 l four-neck flask and methanol is distilled off in the course of 2.5 hours. The mixture is then heated and a mixture of methanol and toluene is distilled off in 1.5 hours at a distillate temperature of 100° C. The residue was transferred to a 3 l stainless steel autoclave, 50 g of methyl chloride were injected and the mixture was heated to 140° C. After 1 hour a further 50 g of methyl chloride were injected, and after 2 hours again 52 g of methyl chloride were injected. The mixture was then stirred for a further 5 hours at 150° C.

The batch was cooled and transferred to a 3 l four-neck stirred flask apparatus equipped with a distillation head. The majority of the toluene was distilled off at atmospheric pressure and the remainder at 33 mbar to a bottom temperature of 90° C. 981 g of 20% strength by weight sulphuric acid was added to the remaining suspension and the mixture was refluxed for 7 hours. The product was then distilled off azeotropically via a water separator (distillate temperature at atmospheric pressure: 92° to 100° C.). 212.5 g of a water-clear product having a content of 77.7% by weight of 2-methylcyclopentanone and 22% by weight of water were obtained. The yield was 84.2%, based on dimethyl adipate used.

If desired, the water can be removed by extraction and/or distillation from the 2-methylcyclopentanone obtained.

What is claimed is:

1. A process for the preparation of a 2-substituted cyclopentanone of the formula

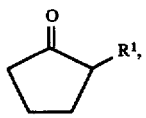 (I)

in which
R$^1$ represents straight-chain or branched C$_1$–C$_6$-alkyl, C$_3$–C$_7$-cycloalkyl or unsubstituted or halogen-substituted C$_7$–C$_{12}$-aralkyl,
in which an adipic ester of the formula

 (II)

in which
the two R$^2$ are identical or different and each represent straight-chain or branched C$_1$–C$_{10}$-alkyl, C$_7$–C$_2$-aralkyl which are unsubstituted or substituted by up to 3 identical or different substituents selected from the group consisting of the halogens and the C$_1$–C$_6$-alkyl, C$_1$–C$_6$-alkoxy and nitro groups, or C$_6$–C$_{10}$-aryl which is unsubstituted or substituted by up to 3 identical or different substituents selected from the group consisting of the halogens and the C$_1$–C$_6$-alkyl, C$_1$–C$_6$-alkoxy and nitro groups,
is reacted in the presence of an inert solvent with an alkoxide of the formula (III)

 (III), in which
M represents an alkali metal or an alkaline earth metal,
R$^3$ represents C$_1$–C$_{10}$-alkyl, C$_3$–C$_{10}$-cycloalkyl or C$_7$–C$_2$-aralkyl and
n, depending on the valency of M, represents 1 or 2,
a salt of the cyclopentanone-2-carboxylic ester of the formula (IV) is thus obtained

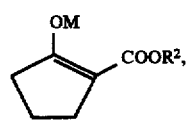 (IV)

in which
R$^2$ has the meaning given under formula (II), and
M represents one equivalent of an alkali metal or alkaline earth metal,
this, without isolation, is alkylated with an alkylating agent of the formula (V),

 (V), in which
R$^1$ has the meaning given under formula (I) and
X represents halogen, C$_1$–C$_6$-alkylsulphonate, or C$_6$–C$_{10}$-arylsulphonate which are unsubstituted or substituted by up to two C$_1$–C$_4$-alkyl groups,
a 2-R$^1$-cyclopentanone-2-carboxylic ester of the formula (VI) is thus obtained

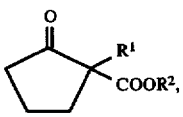 (VI)

in which
R$^2$ has the meaning given under formula (II) and
R$^1$ has the meaning given under formula (I),
and this, without isolation, is hydrolysed and decarboxylated by treating it with an acid and heating to give I in an overall yield of 80% or higher.

2. The process of claim 1, in which in formula (II), the two R$^2$ radicals are identical and represent straight-chain or branched C$_1$–C$_6$-alkyl, benzyl which are unsubstituted or substituted by up to two substituents selected from the group consisting of the halogen atoms and the C$_1$–C$_4$-alkyl groups, or phenyl which is unsubstituted or substituted by up to two substituents selected from the group consisting of the C$_1$–C$_4$-alkyl groups and the nitro group, in formula (III), M represents sodium, potassium, lithium, calcium or magnesium and R$^3$ represents straight-chain or branched C$_1$–C$_6$-alkyl, C$_3$–C$_7$-cycloalkyl or benzyl, as solvent, use is made of an aliphatic or aromatic hydrocarbon having a boiling point of at least 80° C. (at atmospheric pressure) or aromatic hydrocarbons substituted by at least one of halogen and C$_1$–C$_4$-alkoxy, or mixtures of these solvents, and the alkoxide of the formula (III) is used as a solution in the alcohol underlying the respective alkoxide and the alcohol is distilled off before the reaction with the adipic ester of the formula (II) progresses to any significant degree.

3. The process of claim 1, in which a dipolar aprotic solvent is additionally added to the solvent.

4. The process of claim 1, in which, per mol of adipic ester of the formula (II), 0.1 to 10 equivalents of an alkoxide of the formula (III) are used and the reaction is carried out at a temperature in the range of 80° to 200° C.

5. The process of claim 1, in which, as alkylating agent of the formula (V), use is made of one in which R$^1$ represents methyl, ethyl, n-propyl, i-propyl, benzyl, 4-chlorobenzyl or 4-fluorobenzyl and X represents chlorine, bromine or p-tolylsulphonate.

6. The process of claim 1, in which, per mol of adipic ester of the formula (II), 1 to 20 mol of an alkylating agent of the formula (V) are used, the alkylation is carried out at temperatures in the range 0° to 250° C. and, after the alkylation, the solvent and any excess alkylating agent present are removed.

7. The process of claim 1, in which the acid treatment is carried out with hydrobromic acid, sulphuric acid, an alkylsulphonic acid or an arylsulphonic acid and the acid is used in the form of an aqueous solution.

8. The process of claim 1, in which, per mol of adipic acid ester of the formula (II), 1 to 10 equivalents of acid are used.

9. The process of claim 1, in which the prepared 2-substituted 2-cyclopentanone of the formula (I) is isolated by azeotropic distillation.

* * * * *

UNITED STATES PATENT AND TRADEMARK OFFICE
CERTIFICATE OF CORRECTION

PATENT NO. : 5,672,763
DATED : September 30, 1997
INVENTOR(S) : Muller, et al.

It is certified that error appears in the above-indentified patent and that said Letters Patent is hereby corrected as shown below:

Col. 7, lines 20-21  Delete " $C_7$-$C_2$-aralkyl " and substitute -- $C_7$-$C_{12}$-aralkyl --

Col. 7, lines 36-37  Delete " $C_7$-$C_2$-aralkyl " and substitute -- $C_7$-$C_{12}$-aralkyl --

Signed and Sealed this

Ninth Day of June, 1998

Attest:

BRUCE LEHMAN

Attesting Officer    Commissioner of Patents and Trademarks